(12) United States Patent
Garza Alvarez (10) Patent No.: US 7,056,305 B2
(45) Date of Patent: Jun. 6, 2006

(54) INTRAGASTRIC BALLOON ASSEMBLY (76) Inventor: José Rafael Garza Alvarez, Cerrada de San Borja No. 44, Col. Del Valle, Mexico D.F. 03100 (MX)

( * ) Notice: Subject to any disclaimer, the term of this patent is extended or adjusted under 35 U.S.C. 154(b) by 180 days.

(21) Appl. No.: 10/656,219

(22) Filed: Sep. 8, 2003

(65) Prior Publication Data

US 2004/0059289 A1 Mar. 25, 2004

Related U.S. Application Data (63) Continuation-in-part of application No. PCT/MX01/00039, filed on Jun. 21, 2001.

(30) Foreign Application Priority Data

Mar. 9, 2001 (MX) .......................... PA/u/2001/000069 U (51) Int. Cl.
A61M 29/00 (2006.01)

(52) U.S. Cl. .................................... 604/191; 604/96.01
(58) Field of Classification Search .............. 604/96.01, 604/101.01–101.05, 912, 915, 916, 917, 604/918, 919, 920, 921, 97.01, 97.03, 98.01, 604/99.01, 99.02, 99.03, 99.04, 103.11; 606/192–194
See application file for complete search history.

(56) References Cited

U.S. PATENT DOCUMENTS

| | | | |
|---|---|---|---|
| 4,416,267 A | 11/1983 | Garren et al. | |
| 4,723,547 A | 2/1988 | Kullans | |
| 4,739,758 A | 4/1988 | Lai | |
| 4,899,747 A | 2/1990 | Garren et al. | |
| 5,234,454 A | * 8/1993 | Bangs | ........................ 606/191 |
| 5,259,399 A | 11/1993 | Brown | |
| 5,993,473 A | 11/1999 | Chan et al. | |
| 2001/0037127 A1 | 11/2001 | De Hoyos Garza | |
| 2002/0055757 A1 | 5/2002 | Torre et al. | |

FOREIGN PATENT DOCUMENTS

| | | |
|---|---|---|
| EP | 0 137 878 A1 | 4/1985 |
| EP | 0 246 999 A1 | 11/1987 |

* cited by examiner

Primary Examiner—Manuel Mendez
(74) Attorney, Agent, or Firm—Foley & Lardner LLP (57) ABSTRACT This invention combines three medical-surgical elements such as an intragastric balloon, a valve to control the postoperatory inflating and the technique of percutaneous gastronomy with endoscopic control, as well as a new mean to fix the assembly that avoids the balloon migration. The intragastric balloon assembly of the invention comprises the silicone balloon with an inflating catheter and a device consisting in a silicone bar, which will be used as a tension support and for fixation to the aponeurosis by means of an adjustable plate, according to the needs, that may be secured with suture points or with metallic staples to the aponeurosis. Once such elements have been secured, the support is cut and the catheter is connected to an inflating valve, which in a preferred embodiment is placed in subcutaneously and held in place with suture points or staples to the aponeurosis.

50 Claims, 11 Drawing Sheets

INTRAGASTRIC BALLOON ASSEMBLY

FIELD OF THE INVENTION

This invention refers to a kind of medical devices used to reduce the food intake of persons suffering from obesity, specially persons with morbid obesity.

BACKGROUNDS OF THE INVENTION

The exogenous obesity, also named as morbid obesity or other names, generally means a weight increase in a significant proportion according to height, age, etc., that may be a risk for life due to the problems caused by the obesity itself. Before this medical circumstance, diverse medical treatments for weight reduction usually fail, therefore, surgical procedures have remained as the only possibility of treatment with an actual effectiveness, in most of the cases.

The obesity problem is so significant in developed countries that it has been considered as a public health problem, so the most important objective of any therapeutics is trying to solve this ailment with more effective treatments and less complications, less morbi-mortality and lower costs.

During the sixties and seventies, surgical experiences trying to reduce overweight were made and reported, by creating derivations that may produce a short intestine effect, usually having disastrous results, since morbi-mortality was so high that caused almost a total abandonment thereof, until surgical devices appeared such as staplers that arrived to our country at the end of the seventies, early eighties, starting a series of works published throughout the world, mainly about gastroplasties and derivations with a plurality of variations, the results of which were good as to weight control and decrease refer, but open surgery was needed having therefore risks in surgery, anesthesia, etc., in addition to high cost.

More recently, about 5 years ago, a new surgical technique appeared, consisting in placing by laparoscopy, an inflatable band encircling the stomach on its upper part, by means of a subcutaneous valve that may be controlled by radiology and/or endoscopy. Through this technique, a gastric reduction and food intake decrease are produced, resulting in a significant weight loss, practically the same as the one obtained by open surgery with staplers, but with less morbi-mortality and the advantages of the laparoscopic surgery, i.e., less pain and fast postoperative recovery. However, the most important problem of this surgical technique is the cost increase, as it also an hospital, surgical and laparoscopic procedure, in addition to the band cost and experienced surgeons requirement.

At early eighties, the first reports on the use of intragastric balloons for obesity treatment appeared, which partially fill the stomach to produce a feeling of satiety, thus helping to reduce the food intake and to adopt new eating habits. Since then and during the next 10 years, approximately, scientific literature publications of several countries were issued about diverse experiences on the use of balloons made of different materials, most of them reporting failures and very low success percentages, due to many complications and troubles during the placing procedure, handling and surveillance during the treatment period, and therefore, the method lost credibility and in many cases, it was abandoned, except for isolated experiences, reported in diverse publications. Currently, Bioenterics Corporation manufactures and distributes an intragastric balloon named BIB® System, which is seldom used, because the same company recommends it only as an alternative for limited reduction short programs or in some cases, prior to a definitive surgery, for which a gastric capacity reduction surgery via laparascopy is recommended, by applying a gastric band, produced by the same company.

The most significant problems arising from the use of intragastric balloons were, on the one hand, the manufacturing material, because the elements employed at the beginning were easily destroyed by gastric juices, so the balloon should be frequently replaced, however, nowadays this issue has been solved by the use of a resistant silicone material, that is able the stay several months inside the patient. Other important difficulties are the balloon rupture, which consequently causes its migration towards the intestine, eventually causing an intestine obstruction requiring surgery, and also the inflated balloon migration causing injuries to gastric mucous and the esophagus or pylorus obstruction. Even more, the balloons available at the market, show a great technical difficulty for endoscopic placing and the inflating maintenance or modification, once it has been placed into the stomach.

There are several documents describing intragastric balloons with improvements intended to overcome some of these inconveniences, including the one described in U.S. Pat. No. 5,259,399 of Alan Brown, consisting in a balloon that is placed at the stomach fundus by means of a percutaneous gastronomy and it is fixed to the patient's skin, with a rigid or semi-rigid thick device, introducing the balloon there trough which is then inflated and deflated with solutions and controlled by sensors placed on the patient's body and a battery driven electric pump driven placed out of the patient's body. The disadvantage of this device is that patient must suffer a probe or thick catheter out of the abdomen skin and such probe or catheter has to be connected to the inflating or deflating equipment each time any food is ingested, resulting very uncomfortable for the patient.

On the other hand, U.S. Pat. No. 5,234,454 by Roger G. Bangs, describes an intragastric balloon placed through a surgical gastrostomy previously made (several weeks before), to place the balloon later, implying a prior surgery. In addition, the used probe is very thick, approximately 1 cm diameter or more, and it stays externally, which means that the patient must have a probe out of his/her body through a puncture made in the abdominal wall, which, in addition to the inconvenience found in the Alan Brown US Patent, causes constant pain and discomfort to the patient. Bangs' device has two balloons, one to be inflated and maintain the stomach placed against the abdominal wall on the inside and a distal balloon, used to fill the stomach.

Mexican Patent Application No. PA/a/2000/001922, corresponding to U.S. Patent Application No. 2001/0037127 A1 of Andres de Hoyos Garza, describes a catheter of percutaneous, intragastric balloon for obesity treatment, consisting in a modification to the endoscopic percutaneous gastrostomy probe which has been modified in its proximal or intragastric end, by being provided with a balloon that is inflated with air to different volumes through an external or extragastric valve by means of a manometer or syringe. The advantage described by the inventor, compared with the prior art is that, it neither moves in the stomach, nor migrates in the event of rupture as it is fixed, and its filling capacity may be controlled externally at any time. A disadvantage found with this system is that it is fixed to the external side of the stomach wall on the skin, then patient must bear external elements, that may be quite annoying. On the other hand, de Hoyos fails to disclosed the way to fix the system and most important, leaks and infections of stomach wall tissues—due to its communication with the stomach—are not contemplated or any how solved.

Likewise, U.S. Patent Application No. 2002/0055757 of Roger de la Torre et al., discloses a Method and a Device to be used in the Placing of a Minimum Invasive Intragastric Device, such device describes an expandable component and fasteners such as sutures, this device is partially extended through the stomach wall and fastened or anchored in the patient's stomach. The device may be spread out or removed by an transesophageal approach and/or through a combination of transesophageal or transabdominal approaches. This invention fixes the balloon to the stomach and abdominal wall by means of sutures, which may cause tissue necrosis and in a few days leaks, infections or stomach piercing may happen, and once it has been installed within the stomach, the inflating control is not solved.

Likewise U.S. Pat. No. 5,993,473 of Young C. Chang and Mei H. Chan, describes a device of expandable body for gastric cavity, including an elastic expandable body, a rigid and sealed supply filling tube connected to the expandable body and has a fastener and a valve over the base of the supply filling tube. The device proposed by Messrs. Chang and Chan includes several elements disposed outside the abdominal wall with a rigid and wide catheter, which causes great discomfort to the patient and additionally, they do not solve the fixing technique at the abdominal wall.

Therefore, there is a need to have a mean for morbid obesity treatment that reduces the surgical and postoperatory risks, easy to handle and install by a minimum invasive surgery technique, without laparoscopic surgery or any other type, with less anaesthetic or surgical trauma, having an inflating control, producing a significant and controlled weight reduction, similar to current surgical proceedings of gastroplasty derivations and placing of bands, substantially eliminating the discomfort to patient and reducing the current cost of other surgical treatments.

SUMMARY OF THE INVENTION

The object of the present invention is to provide an intragastric balloon assembly that remains fixed to the abdominal wall, avoiding movement and migration of the balloon and therefore any possibility of gastric wall injures resulting from such movement as well as any intestinal obstruction in the event of a balloon rupture.

Even more, the balloon assembly of the invention, intends to avoid the nuisance caused by external elements such as gastrostomy, without the presence of assembly elements out of the patient's body.

Another object of the invention is to cause the patient less anesthesic-surgical trauma while placing the intragastric balloon.

One more object of the invention is to provide a system to inflate the balloon that allows to have an inflating magnitude control during its placement and any time later.

It is also an object of the invention to reduce the cuts on the patient's tissues as well as to reduce the number of fixed elements of the intragastric balloon assembly within the patient's body.

Likewise, other object of the present invention is to provide a balloon that can be manufactured in diverse shapes and having a higher capacity than those currently available, since some overweight persons tend to develop larger stomachs.

In addition, with this invention it is intended to decrease the risks of an open surgery as well as the hospitalization risks and costs, by making a short stay or ambulatory surgery.

Other additional and very significant objective of this invention is to provide a mean to avoid gastric liquid leaks towards the abdominal cavity or wall in the balloon fixing place, eliminating thus any possible contamination and infection, as this would mean the need of removing the system.

These and other objectives are achieved by this invention, that combines: a new intragastric balloon assembly that remains fixed within the patient without visible external elements; a fixing mean avoiding the balloon migration; elements to inflate the balloon when placed within the patient's stomach and to modify its volume any time later; as well as a percutaneous gastrostomy technique with endoscopic control, that eliminates the high costs of a laparoscopic surgery and those related to hospitalization, general anesthesia, etc.

The balloon assembly of this invention consists in a balloon, preferably made of silicon or other material non-corrodible by gastric juices and a rigid support fixedly attached thereto, preferably, integrally formed with the ballon, that will serve as a traction mean to carry the ballon into the gastric cavity and also as a tension support. Said rigid support is fixed to the aponeurosis by a fixing plate that may be secured with suture points or metallic staples. This way, external elements on the abdomen skin are avoided, such as thick probes or trocars that are uncomfortable for the patient and also are difficult to control, and susceptible to infection.

Likewise, the invention contemplates providing a mean to inflate the balloon, consisting in an inflating catheter fixedly attached to the balloon in a point adjacent to the rigid support and preferably attached to such rigid support along its length in a detachable way, to suply a fluid to the balloon so as to inflate it at a predetermined volume. Said catheter is separated from the rigid support once the intragastric balloon is disposed within the stomach and then connected to an inflating valve that is subcutaneously fixed and secured to the aponeurosis with suture points or staples, said inflating valve controling the size of the intragastric ballon after placing.

As one of the objects of the invention is to reduce the cuts on the patient's body, as well as the fixed elements of the intragastric balloon assembly, and considering that the above described embodiment of the invention contemplates that the rigid support is attached to a plate subcutaneously fixed while the inflating catheter is connected to a valve also subcutaneously and separately placed through the same or other incision in the abdominal wall, in an additional embodiment of the invention, an element is provided allowing to integrate the fixing plate and the inflating valve, in a way such that, in a preferred embodiment, a tubular device is placed at the center of the valve, to pass the rigid support there through, having also a flange on the superior side of the plate that allows to suture and fix the rigid support to the plate uder some tension.

In an additional effort to reduce the fixed elements in the intragastric balloon assembly of the invention, a third embodiment contemplates to dispose the inflating catheter, detachably joined to the balloon at a position distal from the rigid support, preferably at a diametrically opposed position, where an auto-sealable inflating valve is also provided, over the balloon. This way, the balloon is initially inflated through the catheter, in a way similar to some currently available balloons, but once the balloon has been fixed into the stomach by means of the rigid support and the fixing plate, in the above described way, an easier handling of the balloon is allowed for any later inflating or deflating process during the course of the treatment, being orally made by endoscopy through the esophagus, therefore, such processes are carried out in a faster way, causing minor inconveniences to the patient.

In order to comply with the objective to avoid leaks of the gastric content towards tissues, in an additional embodiment of the invention, a mean to favor the fibrosis and cicatrization of the stomach wall at the perforation point for balloon fixation is provided, promoting this way the attachment of the assembly to the abdominal wall at the peritoneal layer, such mean consists in a layer of a material promoting fibrosis and cicatrisation such as goretex, mersilene or the like, applied over the rigid support and the base of the balloon, that is the site where rigid support emerges, which are in contact with the stomach wall and the abdominal wall, up to the aponeurosis.

Even more, to allow a better adherence of the balloon to the stomach and of the stomach to the abdominal wall, a further embodiment of the invention contemplates providing a circular reinforcement made of the same material as the balloon, disposed adjacent to the base of the balloon, that is, the point where the rigid support emerges, integrally formed with the balloon, such circular reinforcement consisting in a disk having embossments formed thereon radially distributed at the edge thereof for the purpose of not interrupting blood circulation of the tissue in contact with the intragastric balloon and other elements of the assembly, avoiding any possibility of necrosis in that area of the stomach.

Likewise, in a more preferred embodiment of the invention, the intragastric balloon assembly also includes a circular foldable plastic screen, made of a material such as soft silicon, disposed over and integrally made with the rigid support, which spreads out within the abdominal cavity similar to an umbrella, laying such screen over the stomach external wall and on the peritoneum, adhered in a circular area beside the balloon base, thus perfectly sealing the area of the hole made in the stomach. Such plastic screen formimg a layer that avoids leakage of gastric juices that may cause greater complications, such as bacterial infection, in both the abdominal cavity and abdominal wall.

DETAILED DESCRIPTION OF THE INVENTION

Figure 1:
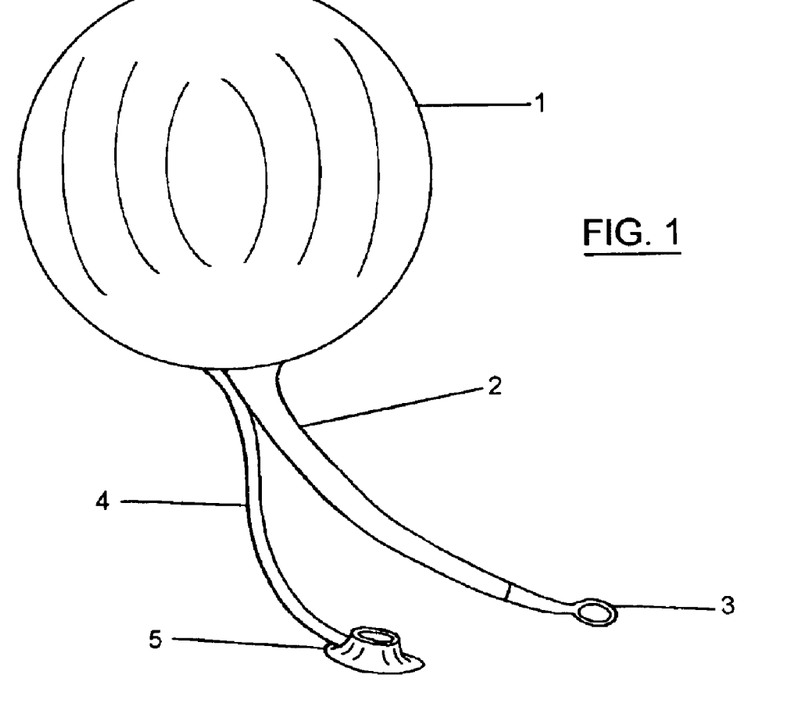
FIG. 1 shows the intragastric balloon assembly of the invention according to a first embodiment.

The intragastric balloon of the invention, shown in FIG. 1, consists in a balloon 1, preferably made of a distensible elastic silicone, and a capacity between 200 to 1000 c.c. approximately, which may have a circular form (as shown in FIG. 1) or d or kidney like form. Said balloon 1 is provided with a rigid support 2, used as guideline and support thereof, consisting in a lengthened element such as a solid tube preferably made of silicone, unitary fixed to balloon 1 and having a diameter such that it is larger at the end joined to balloon 1 and becomes smaller towards the opposite end where a handle 3 is located to hold it in place. Likewise, such rigid support 2 has a groove (not shown) extended through its length from the end attached to the balloon 1 up to approximately 15 cm ahead, disposed to receive the inflating catheter 4, which is attached to support 2 and may be easily detached from it. Said inflating catheter 4 has a diameter of approximately 1.5 to 2.0 mm and a length of approximately 20 cm.

Likewise, the assembly of the invention comprises an inflating valve 5 which is a rigid plastic or silicone safety valve having a 2 cm diameter and 1 cm height, approximately, which is easy available in the market and has two or three fixing flanges (not shown). Said inflating valve 5 is attached to the inflating catheter and fixed to the aponeurosis.

Figure 2:
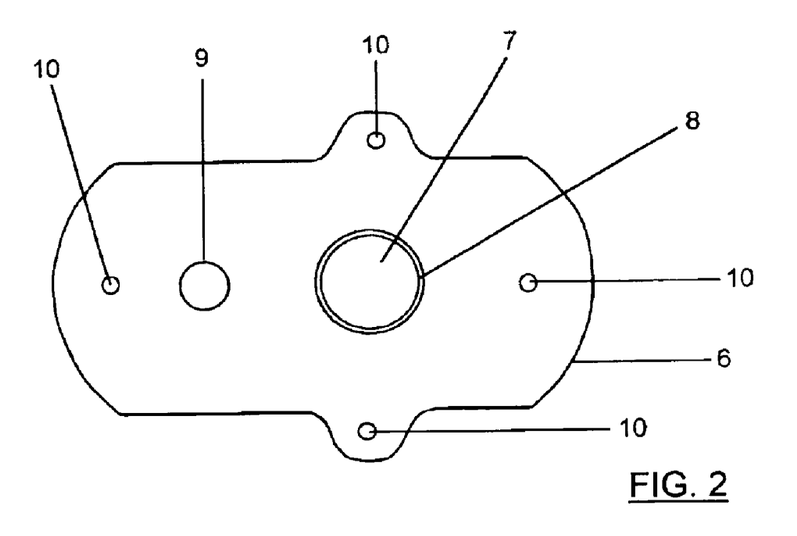
FIG. 2 shows a flat upper view of the fixing plate of the balloon assembly of this invention.
Figure 3:
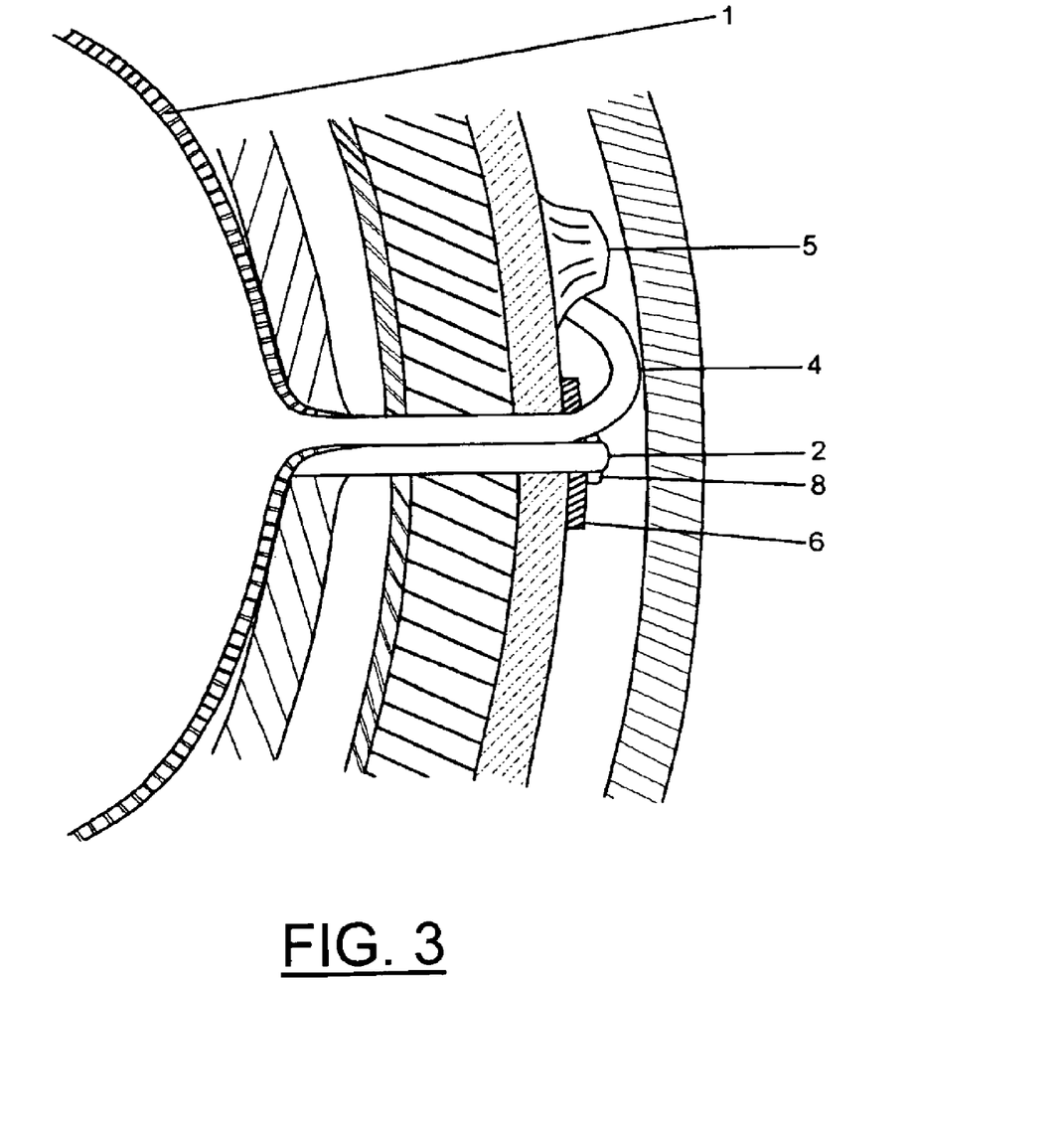
FIG. 3 is a scheme that shows how the intragastric balloon assembly is implanted.

In addition, the balloon assembly of the invention, includes a fixing plate 6, shown in detail in FIG. 2, which is a plate of approximately 1 to 1.5 mm wide and preferably made of high hardness inert silicone or plastic shown in a rectangular shape with rounded corners, but this may be different, either circular, ovoid, etc. and its diameter is about 4 to 5 cm approximately. Said fixing plate 6, has a first hole 7 having a circular flange 8, which is adjusted and fixed to rigid support 2 and a second hole 9, to pass inflating catheter 4 there through, and also including several fixing holes 10, preferably being disposed 4 of those holes.

Figure 12:
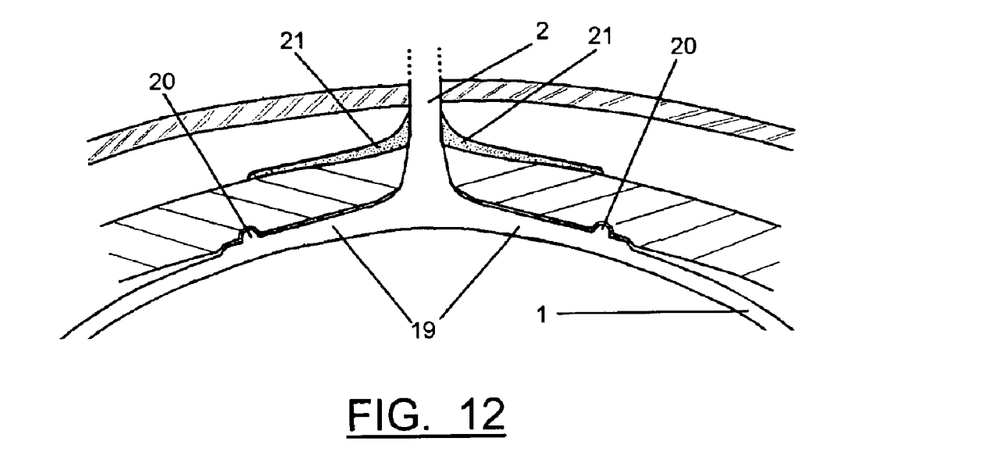
FIG. 12 is a cross section view of the scheme in FIG. 11 at the point where balloon 1 base is attached to the stomach wall showing the disposition of the embossements in balloon 1 base.
Figures 13, 14, 15:
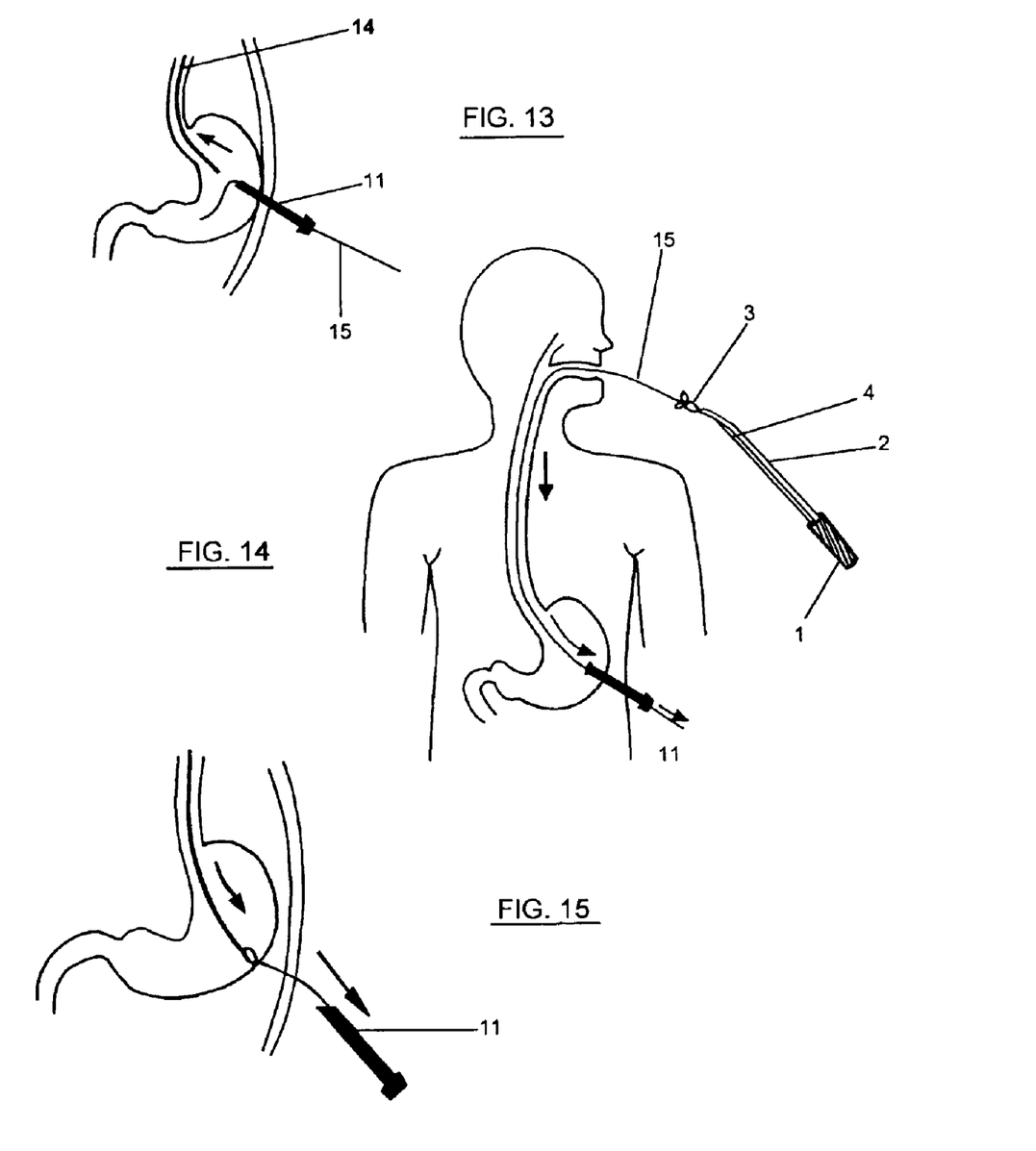
FIGS. 13 to 15 illustrate the surgical technique to implant the intragastric balloon assembly of the invention.

Implantation of the intragastric balloon assembly of the invention (see FIGS. 12, 13 and 14) is made by introducing a central view flexible endoscope (14) through the mouth of the patient to identify the stomach, which is inflated with air by means of the endoscope, then the bottom of the gastric body is pressed against the major curvature with the endoscope, to identify the puncture site by locating the light through the abdominal wall, then a puncturing trocar (11) is introduced at the puncturing site, by piercing all layers of the abdominal wall and perforating the stomach, watching this operation through the endoscope, so that a gap is formed for the traction of rigid support 2 along with catheter 4 and ballon 1, which is carried out with the help of a suture thread 15 that is introduced through trocar 11, once the pointed mandrin has been removed from trocar 11 and is taken out by the pliers of endoscope 14, as illustrated in FIG. 13, and then is pulled out by the endoscope through the oral cavity, where it is secured to handle 3 of rigid support 2, (see FIG. 14). Then, traction of suture 15 is started by pulling it through the abdominal wall so that rigid support 2 along with the catheter 4 and balloon 1 are carried throughout the digestive tube to the patient's stomach, rigid support 2 and inflating catheter 4 being taken through the gastric wall and the abdominal wall. Fixation and placing of intragastric balloon is started by separating catheter 4 from rigid support 2, then rigid support 2 is introduced in hole 7 of fixing plate 6, having removing handle 3; balloon 1 is inflated through catheter 4 to a predetermined volume. Catheter 4 is fixed by passing through hole 9 of fixing plate 6 and joining it to inflating valve 5, fixing in turn the fixing plate and inflating valve to anterior aponeurosis of abdomen with suture points or staples.

In addition, to reduce the number of incisions in the patient's body, as well as the fixed elements of the intragastric balloon assembly, a second embodiment of the invention contemplates simplifying the way to fix the rigid support 2 and catheter 4, which consist in providing an integrated fixing plate 6' having a hole 7' to fix rigid support 2 and an inflating valve 5' fixedly disposed thereon, eliminating the need to have two fixed elements subcutaneously disposed.

Figure 4A:
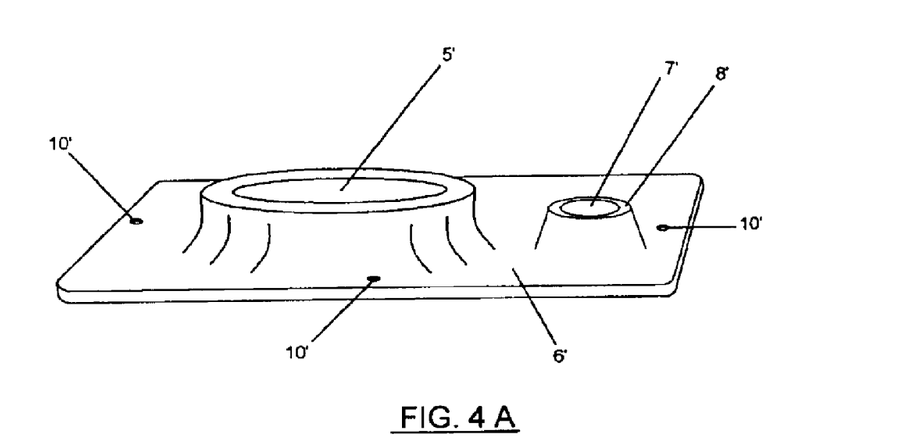
FIGS. 4A and 4B are a perspective lateral view and a flat superior view, respectively, of an arrangement of the inflating valve integrated with the fixing plate of the intragastric balloon assembly according to a second embodiment of this invention.
Figure 4B:
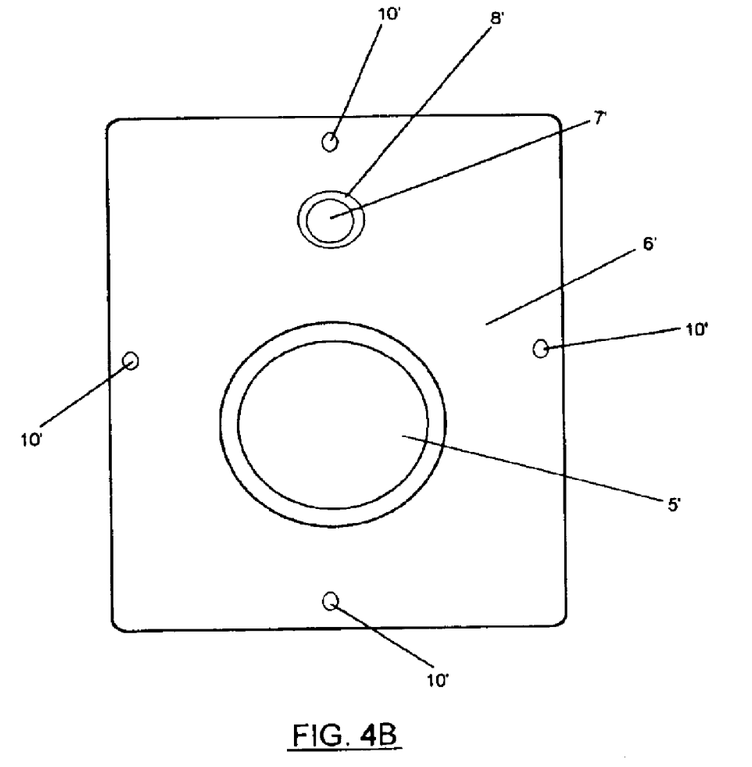

A first arrangement of the integrated plate 6' is shown in FIGS. 4A and 4B, which comprises a fixing plate 6' having a hole 7' with a circular flange 8' formed therein and a valve 5' contiguously disposed thereon, so that inflating catheter 4 is fixed by the inferior side of plate 6' to valve 5' and rigid support 2 is passed through hole 7' and is fixed to circular flange 8'. Moreover, in this arrangement, a wider bilobate fixing plate is contemplated, such that one of the parts will serve to fix the plate, and the other is integral with inflating valve 5".

Figure 5A:
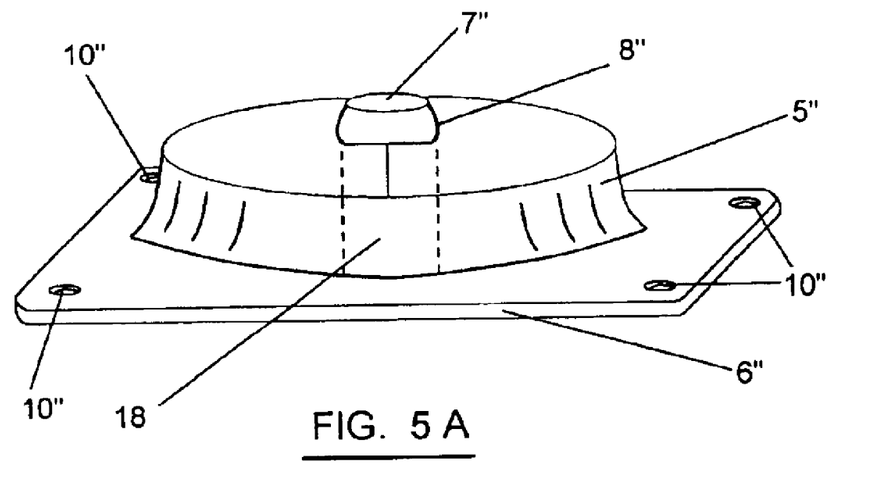
FIGS. 5A and 5B are a perspective lateral view and a flat superior view, respectively, of a second arrangement of the inflating valve integrated with the fixing plate of the intragastric balloon assembly according to a second embodiment of this invention.
Figure 5B:
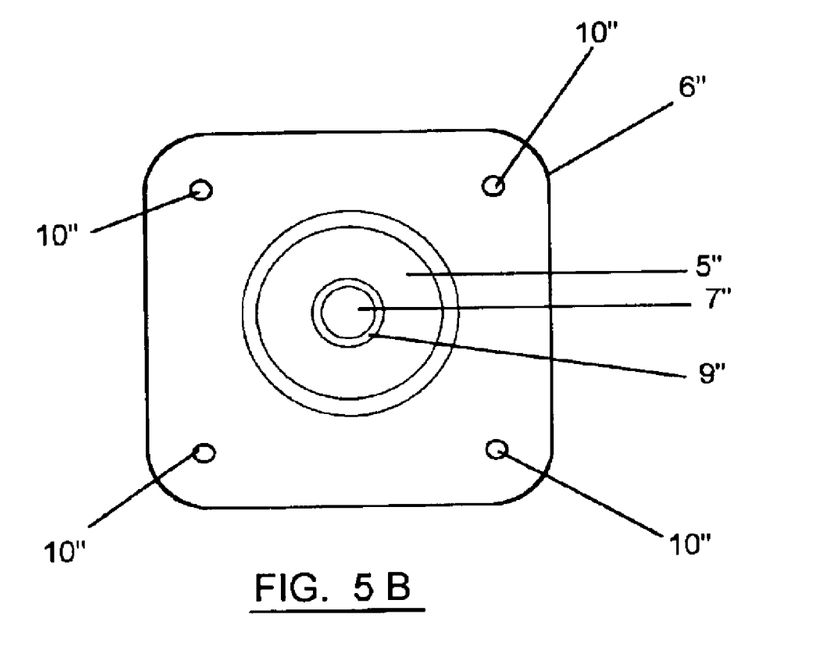
Figure 6:
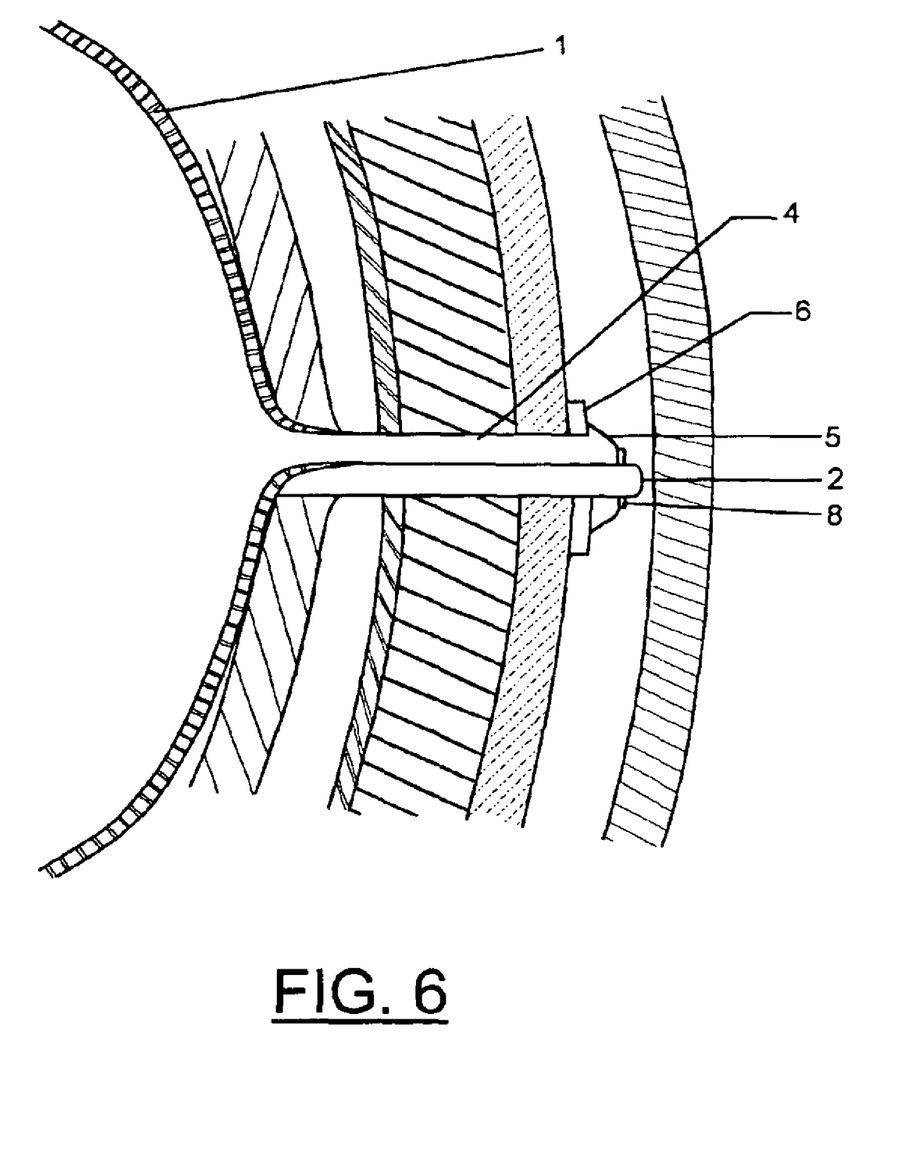
FIG. 6 is a scheme illustrating how the intragastric balloon assembly has been implanted according to a second embodiment of this invention.
Figure 7:
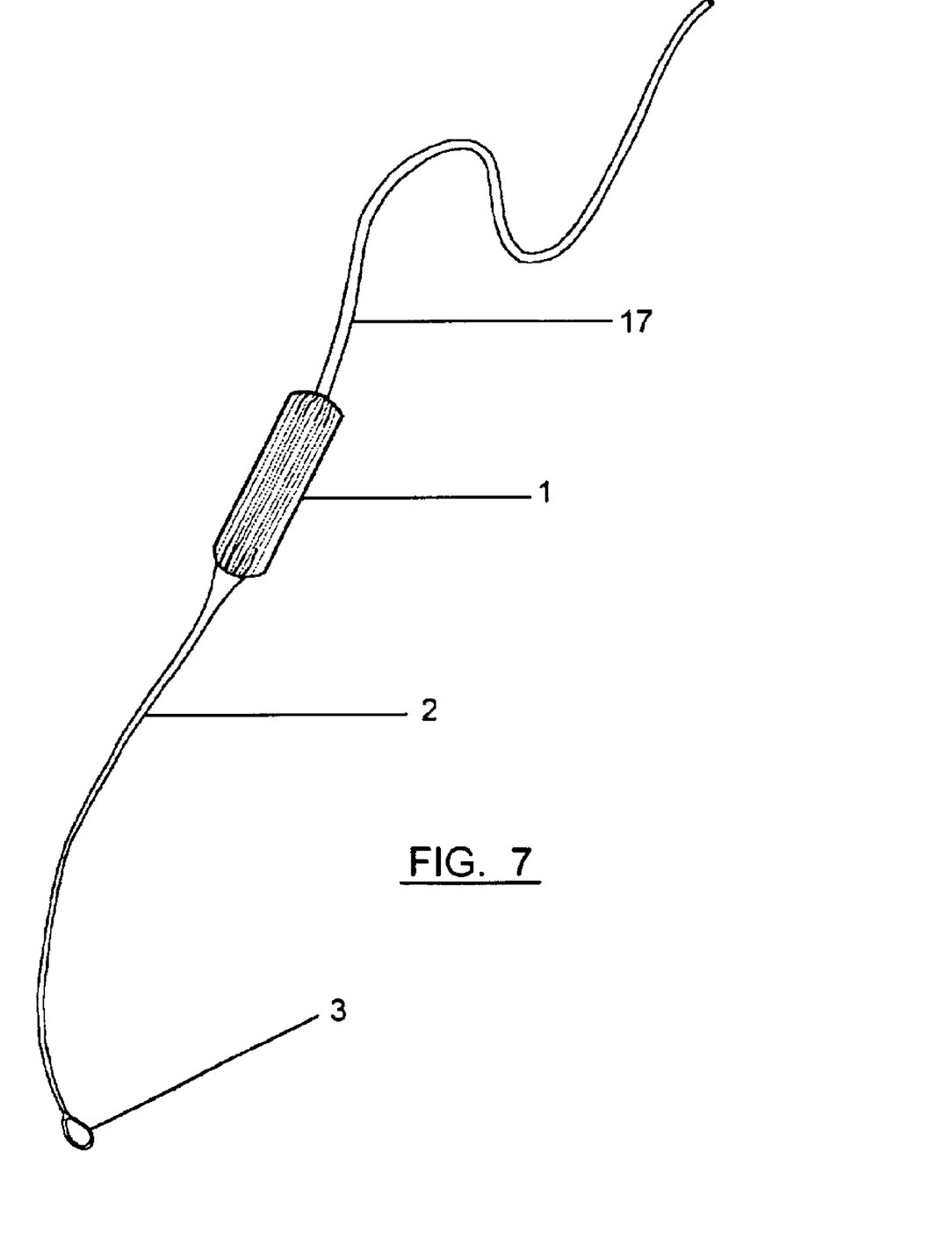
FIG. 7 shows the deflated intragastric balloon assembly according to a third embodiment of the invention.

A second arrangement of integrated fixing plate 6" is shown in FIGS. 5A and 5B, which additionally includes a tubular element 18 disposed at the center of valve 5", so that rigid support 2 passes through said tubular element 18, said plate 6" also having a flange 8" on the upper side thereof, to suture and fix rigid support 2 to plate 6" under some tension.

Figure 8:
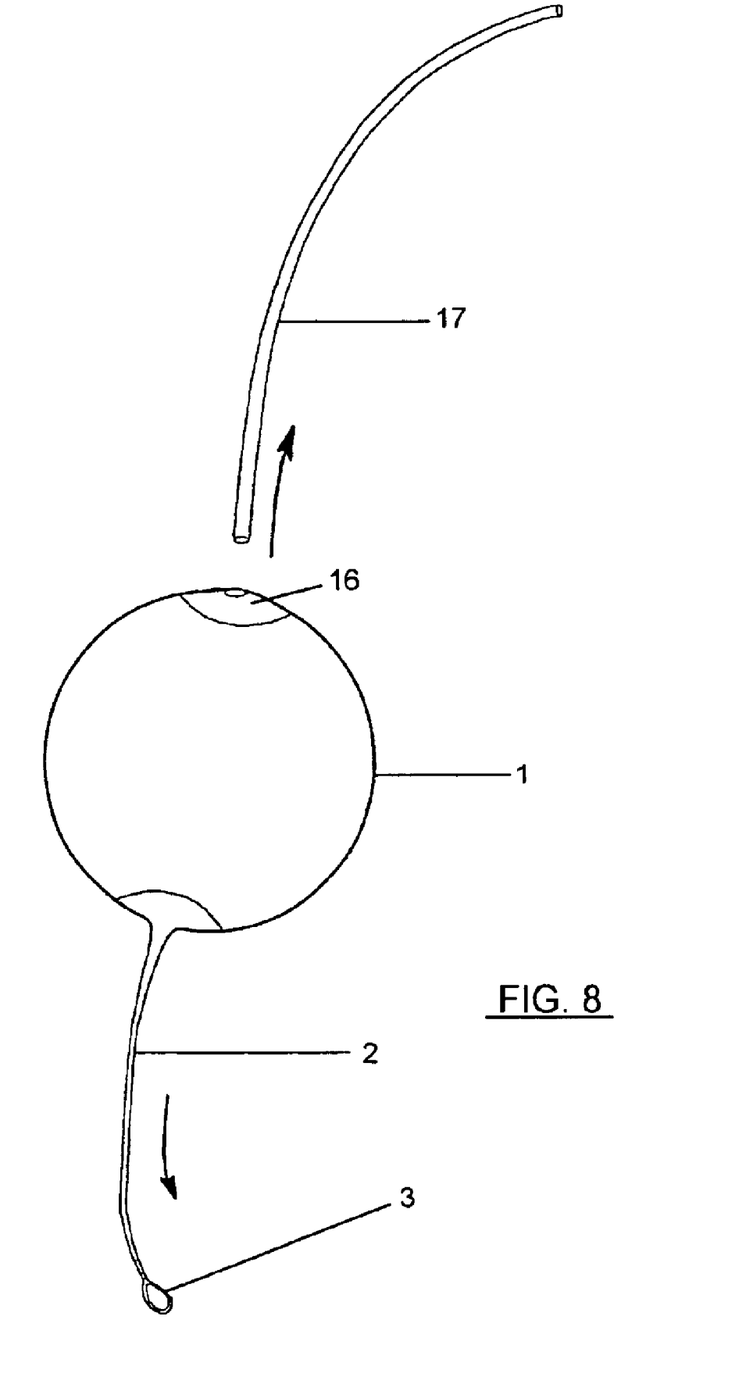
FIG. 8 shows the intragastric balloon assembly of FIG. 7 in its inflated form with the inflating catheter detached.
Figure 9:
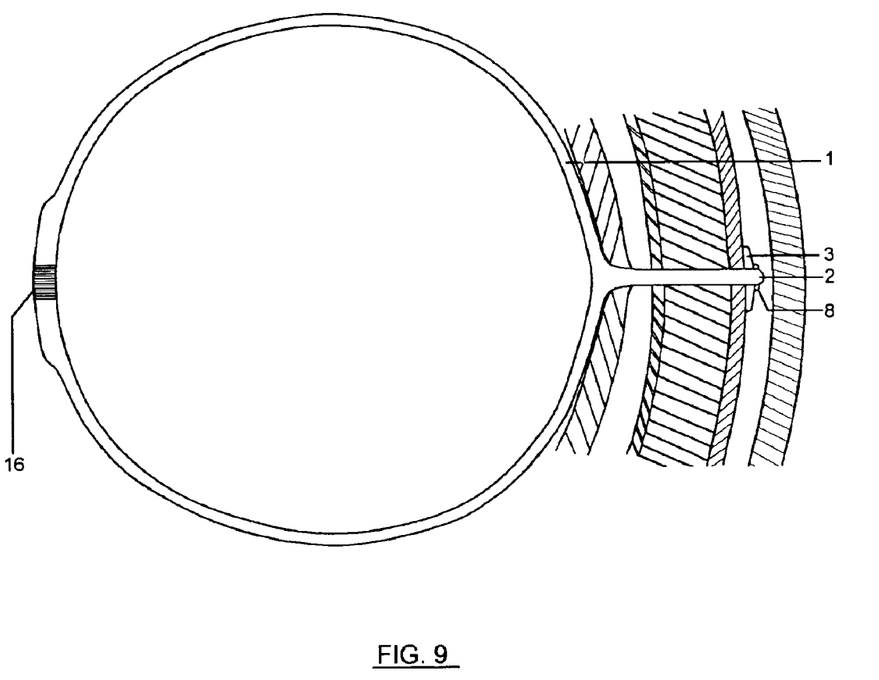
FIG. 9 is a scheme illustrating how the intragastric balloon assembly of FIG. 7 has been implanted.

In a third embodiment of the invention, the intragastric balloon assembly includes a balloon 1, and a rigid support 2 just as in the above described embodiments, that serves as guideline and support for balloon 1, consisting in a lengthened element, such as a solid tube preferably made of silicon, that is unitarily fixed to balloon 1, and having a diameter longer at the end joined to balloon 1 which becomes smaller toward the opposite end, where a handle 3 is formed. Moreover, balloon 1 is provided with a self sealing valve 16 fixedly attached to balloon 1, and connected to catheter 17 for an initial inflating of balloon 1, said catheter 17 being detachably joined to balloon 1, in order to be detached from balloon 1 after completing inflatiing, that is when located within the stomach and before fixing the balloon to the stomach wall. Valve 16 is disposed at a point distant from rigid support 2, preferably in a point diametrically opposed to rigid support 2, as better seen in FIG. 8.

Likewise, intragastric balloon assembly of the third embodiment is provided with a fixing plate 6 similar that shown in FIG. 2, which is a plate of approximately 1 to 1.5 mm wide, and is preferably made of silicon or inert plastic of higher hardness and having a diameter preferably between 4 to 5 cm approximately. Said fixing plate 6, has a first hole 7 having a circular flange 8, which is adjusted and fixed to rigid support 2 and also including several fixing holes 10, preferably being disposed 4 of those holes.

Implantation of the intragastric balloon assembly according to the third embodiment of the invention is made by introducing a central view flexible endoscope (14) through the mouth of the patient to identify the stomach, which is inflated with air by means of the endoscope, then the bottom of the gastric body is pressed against the major curvature with the endoscope, to identify the puncture site by locating the light through the abdominal wall, then a puncturing trocar (11) is introduced at the puncturing site, by piercing all layers of the abdominal wall and perforating the stomach, watching this operation through the endoscope, so that a gap is formed for the traction of rigid support 2 along with catheter 4 and ballon 1, which is carried out with the help of a suture thread 15 that is introduced through trocar 11, once the pointed mandrin has been removed from trocar 11 and is taken out by the pliers of endoscope 14, as illustrated in FIG. 13, and then is pulled out by the endoscope through the oral cavity, where it is secured to handle 3 of rigid support 2, (see FIG. 14). Then, traction of suture 15 is started by pulling it through the abdominal wall so that rigid support 2 along with balloon 1 and catheter 17 are carried throughout the digestive tube to the patient's stomach, rigid support 2 being taken through the gastric wall and the abdominal wall. Then an initial inflating is started through the detachable catheter 17, that is partially exposed at that time through the patient's mouth. Said inflating may be not the final, but a partial or temporary, with about 200 to 300 cc of air or other fluid, that allows exerting tension between the rigid support 2 and the inflated balloon 1, so that the perforated stomach wall is closed to the parietal peritoneum layer. Then, traction of the rigid support (2) is made for the balloon (1) to be perfectly attached to the gastric wall and the gastric wall in turn to be adhered to abdominal wall at the peritoneal layer to avoid leakage of gastric content towards the abdominal wall. After that, fixing plate (6) is set introducing the rigid support (2) through the major hole (7) which is secured to circular flange (8) by suture and fixing plate (6) is fixed to the anterior aponeurosis of the abdomen with suture and finally the subcutaneous cellular tissue and the skin are closed.

Figure 10:
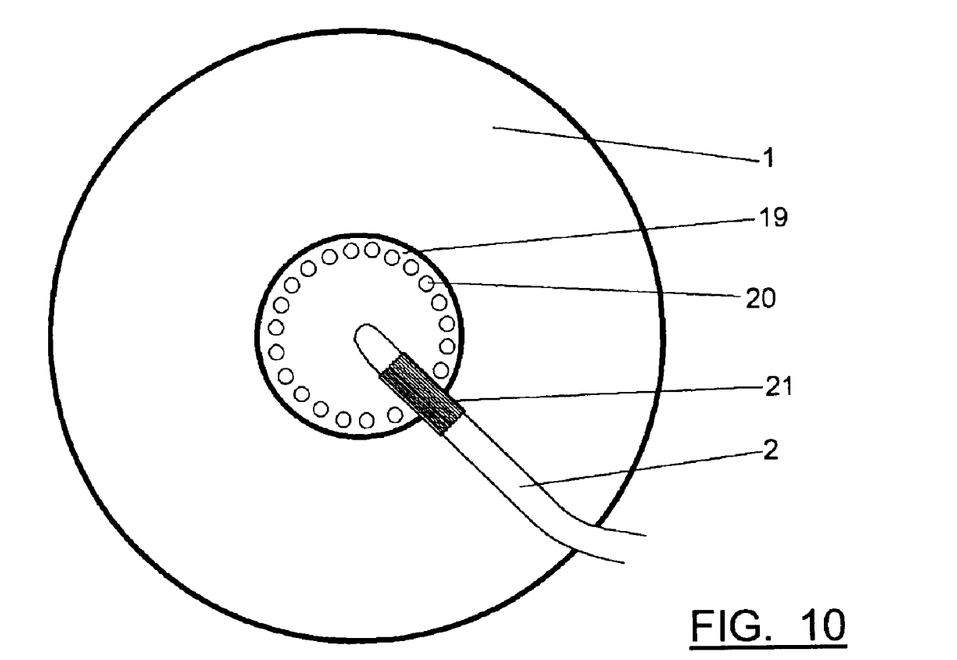
FIG. 10 shows an intragastric balloon assembly, seen the balloon base, according to a fourth embodiment of this invention, showing the balloon inflated.
Figure 11:
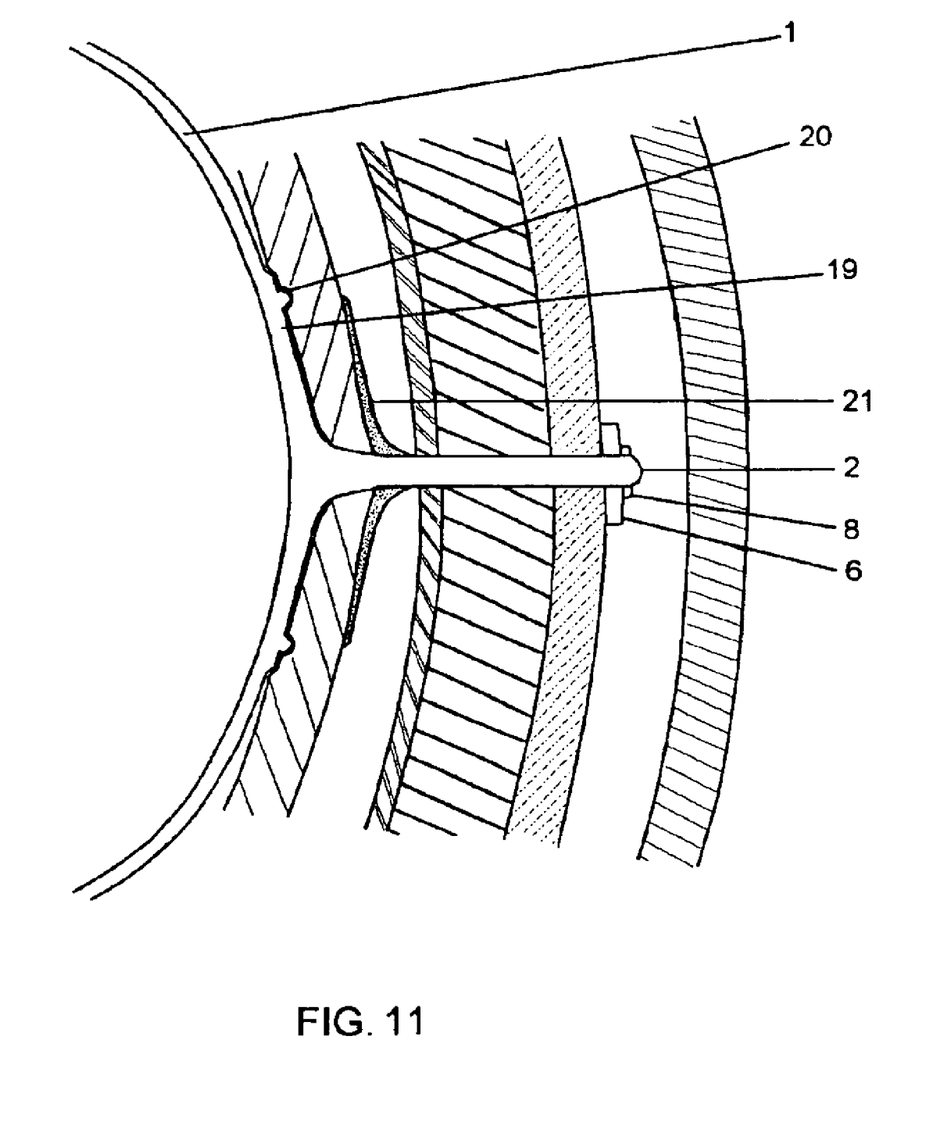
FIG. 11 is a scheme illustrating how the intragastric balloon assembly has been implanted according to the fourth embodiment of this invention.

To prevent leakage of gastric content to abdominal wall, that may have as consequence an infection, a fourth embodiment of the invention, illustrated in FIGS. 10 to 12, contemplates providing balloon 1 with a circular reinforcement 19 integrally formed with balloon 1 and made of the same material as balloon 1, disposed adjacent to the base of balloon 1, that is, arround the point where the rigid support 2 emerges, said reinforcement 19 having a plurality of embossments 20 formed thereon radially distributed at the edge thereof for the purpose of not interrupting blood circulation of the tissue in contact with the intragastric balloon 1 and the elements integrating the assembly, avoiding any possibility of necrosis in that area of the stomach.

This embodiment of the invention also contemplate the provision of a foldable plastic screen 21, made of a flexible material such as soft silicon, disposed around rigid support 2 and spaced apart from balloon 1, integrally formed with rigid support 2. Said screen 21 being initially in a folded position shown in FIG. 10, i.e., before inserting the balloon assembly to the stomach, and it is spread out once it has crossed the stomach wall similarly to an umbrella, said screen 21 laying over the external stomach wall and attaching thereon, so as to seal the area of the hole formed in the stomach and along with circular reinforcement 19 provide an internal and external sealing system, that prevents gastric juices from leaking, that may cause a great complication such as a bacteria infection.

In an additional embodiment of the invention, a mean to favor the fibrosis and cicatrization of the stomach wall at the perforation point is provided, promoting this way the attachment of the assembly to the abdominal wall at the peritoneal layer, such mean consists in a layer of a material promoting fibrosis and cicatrisation such as goretex, mersilene or the like, applied over rigid support 2 and the base of the balloon 1, that is the site where rigid support 2 emerges, which are in contact with the stomach wall and the abdominal wall, up to the aponeurosis so that said tissues are adhered to the elements of the balloon assembly, avoiding this way gastric juice leakage and the related complications. Said fibrosis and cicatrisation promoting material being applied to the balloon 1 base and rigid support 2, once they have been taken to the stomach of the patient.

It will be evident for those skilled in the art that many modifications or variations may be made to the invention herein described without separating from spirit and scope of the same, therefore, it will be understood that what has been described and shown is merely illustrative of the invention and not restrictive thereto.

What is claimed is:

1. An intragastric balloon assembly for reducing the food intake of a person suffering from obesity, the intragastric balloon assembly comprising:
    a balloon made of an acid resistant distensible material;
    an inflating catheter joined at one end to the balloon and configured to inflate the balloon;
    a rigid support including an elongated element formed unitarily with the balloon and having a diameter that is larger at an end joined to the balloon and becomes smaller towards an opposing end, said rigid support being configured for use as a guideline and tractor to introduce the balloon into a stomach through a mouth and as a support to maintain the balloon in a substantially fixed position, said rigid support having a groove along a length of the rigid support from the end joined to the balloon and extending up to approximately 15 cm from the end joined to the balloon;
    a handle disposed at the opposing end of the rigid support and formed unitarily with the rigid support to permit said rigid support to be held during surgery;
    said inflating catheter being fixedly joined at one end to the balloon proximate the rigid support and housed along at least a portion of the length of the inflating catheter within the groove of the rigid support, and configured to be carried along with the rigid support when the assembly is introduced into the stomach and to be detachable from the rigid support for fixation;
    an inflating valve configured to at least one of inflate and deflate the balloon that is joined to the inflating catheter and that has at least two flanges for fixation; and
    a fixing plate having a first hole with a circular flange formed therein which is configured to adjust and fix the rigid support, a second hole that receives the inflating catheter, and a plurality of fixation holes configured to join the plate by at least one of suture stitches and staples to abdominal tissue.

2. An intragastric balloon assembly according to claim 1, wherein the capacity of the balloon is about 200 to 1000 c.c.

3. An intragastric balloon assembly according to claim 1, wherein the balloon has a substantially circular shape.

4. An intragastric balloon assembly according to claim 1, wherein the balloon has a substantially bilobate shape.

5. An intragastric balloon assembly according to claim 1, wherein the balloon has a substantially kidney shape.

6. An intragastric balloon assembly according to claim 1, wherein the rigid support is made of silicone.

7. An intragastric balloon assembly according to claim 1, wherein the inflating catheter has diameter of about 1.5 to 2.0 mm and a length of approximately 20 cm.

8. An intragastric balloon assembly according to claim 1, wherein the fixing plate has a thickness of approximately 1.5 mm, and is made of at least one of silicone and inert plastic of higher hardness.

9. An intragastric balloon assembly according to claim 1, wherein the fixing plate has a shape selected from circular, ovoid and squared.

10. An intragastric balloon assembly according to claim 1, wherein the fixing plate and inflating valve are disposed in a single integrated plate.

11. An intragastric balloon assembly according to claim 10, wherein the integrated fixing plate has the circular flange and the inflating valve contiguously disposed thereon, so that the inflating catheter can be fixed by an inferior side of the fixing plate to the inflating valve and the rigid support can be passed through the hole and fixed to the circular flange.

12. An intragastric balloon assembly according to claim 10, wherein the integrated fixing plate has the inflating valve, the first hole, and a tubular element disposed at the center of the inflating valve, so that the rigid support can be passed through said tubular element; and the flange on an upper side of the inflating valve to suture and fix the rigid support under tension.

13. An intragastric balloon assembly according to claim 1, wherein the rigid support and the balloon are partially covered by a layer of a material configured to promote fibrosis and cicatrisation in regions that will contact tissues.

14. An intragastric balloon assembly according to claim 13, wherein the fibrosis and cicatrisation promoting material is selected from goretex and mersilene.

15. An intragastric balloon assembly according to claim 1, further comprising a circular reinforcement disposed adjacent to a base of the balloon where the rigid support emerges, integrally formed with the balloon and having a plurality of embossments formed thereon radially distributed on an edge thereof, said circular reinforcement being configured to be adhered to an inner wall of the stomach, when setting the balloon assembly in place, to seal a hole formed therein.

16. An intragastric balloon assembly according to claim 15, wherein the circular reinforcement is made of the same material as the balloon.

17. An intragastric balloon assembly according to claim 15, further comprising a foldable plastic screen disposed around the rigid support and spaced apart from the balloon, and integrally formed with the rigid support, said foldable plastic screen being capable of being initially in a folded position, before inserting the balloon assembly into the stomach, and capable of being spread out after crossing the stomach wall, said screen being configured to lay over a stomach external wall and attach thereon to seal an area of the hole formed in the stomach to prevent gastric juices from leaking.

18. An intragastric balloon assembly according to claim 17, wherein the foldable plastic screen is made of silicon.

19. A surgical procedure to set the intragastric balloon of claim 1 to treat a patient suffering from obesity, comprising the steps of:
    applying asepsis and antisepsis measures;
    anesthetizing the patient under an anesthesiologist surveillance;

placing the patient in a ventral decubitus position;

performing an abdomen antisepsis;

setting sterile fields to limit superior hemiabdomen;

introducing a central view flexible endoscope through a mouth of the patient;

identifying the stomach inflated with air by means of the endoscope;

pressing the bottom of a gastric body against the major curvature with the endoscope, to identify a puncture site by locating light through the abdominal wall;

applying local anesthesia with diluted xilocaine without epinephrine at a puncturing site;

making a small incision with a 2 mm knife;

introducing a puncturing trocar at the puncturing site, by piercing all layers of the abdominal wall and perforating the stomach, watching this operation through the endoscope;

removing a pointed mandrin from trocar;

introducing into the stomach a resistant suture through the light of trocar;

taking the suture with the pliers of an endoscope and taking away the endoscope together with the suture through the mouth;

tying the suture to the handle of the rigid support;

making traction of the suture through the abdominal wall so that rigid support along with the catheter and the balloon are carried throughout the digestive tube to the stomach, the rigid support and inflating catheter being taken through the gastric wall and the abdominal wall;

removing the percutaneous trocar;

carrying out a surgical incision of 5–7 cm;

cutting the skin and cellular tissue up to the aponeurosis;

dissecting aponeurosis surface to place the fixing plate on this site;

separating the inflating catheter from the rigid support and cutting the a tip of the rigid support;

inflating the balloon with a fluid;

making traction of the rigid support for the balloon to be attached to the gastric wall and the gastric wall in turn to be adhered to abdominal wall at the peritoneal layer to avoid leakage of gastric content towards the abdominal wall;

fixing the rigid support and introducing it through the first hole, cutting excess of the rigid support and fixing it to the flange by a suture;

fixing the inflating catheter by passing it through a hole of fixing plate, close to the level of the plate flange; cutting the inflating catheter and connecting the inflating catheter to the inflating valve;

fixing the fixing plate to the anterior aponeurosis of the abdomen by suture through fixing holes;

setting the inflating valve in adjoining way to the incision, perforating the cellular tissue at a distance of 5–6 cm from outside and fixing it to the aponeurosis with suture and;

closing the subcutaneous cellular tissue and the skin.

20. A surgical procedure according to claim 19 including the step of applying a layer of a material promoting fibrosis and cicatrisation over rigid support and the balloon on the regions having contact with the tissues, once they have been taken to the stomach of the patient.

21. A surgical procedure according to claim 19 including the steps of:

spreading out the foldable screen once the area of rigid support bearing screen has crossed the stomach wall, so that said screen lays over the stomach external wall and is attached thereon sealing the area of the hole formed in the stomach to prevent gastric juices from leaking.

22. An intragastric balloon assembly for reducing the food intake of a person suffering from obesity, in the intragastric balloon assembly comprising:

a balloon made of an acid resistant distensible material;

an inflating catheter joinable at one end to the balloon and configured to inflate the balloon;

a rigid support including an elongated element formed unitarily with the balloon and having a diameter that is larger at an end joined to the balloon and becomes smaller towards an opposing end, said rigid support being configured for use as a guideline and tractor to take the balloon into a stomach through a mouth and as a support to maintain the balloon in a substantially fixed position, said rigid support having a handle disposed at the opposing end of the rigid support and formed unitarily with the rigid support to permit said rigid support to be held during surgery;

said inflating catheter being detachably joined to the balloon to permit the inflating catheter to be detached from the balloon after inflating;

an inflating valve disposed at a point distant from the rigid support, fixedly attached to the balloon, and connected with detachable catheter for an initial inflating of the balloon; and a fixing plate having a first hole with a circular flange configured to adjust and fix the rigid support and a plurality of fixation holes to join the plate to abdominal tissue.

23. An intragastric balloon assembly according to claim 22, wherein the capacity of the balloon is about 200 to 1000 c.c.

24. An intragastric balloon assembly according to claim 22, wherein the balloon has a substantially circular shape.

25. An intragastric balloon assembly according to claim 22, wherein the balloon has a substantially bilobated shape.

26. An intragastric balloon assembly according to claim 22, wherein the balloon has a substantially kidney shape.

27. An intragastric balloon assembly according to claim 22, wherein the rigid support is made of silicone.

28. An intragastric balloon assembly according to claim 22, wherein the inflating catheter has diameter of about 1.5 to 2.0 mm and a length of approximately 20 cm.

29. An intragastric balloon assembly according to claim 22, wherein the fixing plate has a thickness of approximately 1.5 mm, and is made of at least one of silicone andinert plastic of higher hardness.

30. An intragastric balloon assembly according to claim 22, wherein the fixing plate has a shape selected from circular, ovoid and squared.

31. An intragastric balloon assembly according to claim 22, wherein the inflating valve is disposed in a point diametrically opposed to the rigid support.

32. An intragastric balloon assembly according to claim 22, wherein the rigid support and the balloon are partially covered by a layer of a material configured to promote fibrosis and cicatrisation in regions that will contact tissues.

33. An intragastric balloon assembly according to claim 32, wherein the fibrosis and cicatrisation promoting material is selected from goretex and mersilene.

34. An intragastric balloon assembly according to claim 22, further comprising a circular reinforcement disposed adjacent to a base of the balloon where the rigid support emerges, integrally formed with the balloon and having a plurality of embossments formed thereon radially distributed on an edge thereof, said circular reinforcement being configured to be adhered to an inner wall of the stomach, when setting the balloon assembly in place, to seal a hole formed therein.

35. An intragastric balloon assembly according to claim 34, wherein the circular reinforcement is made of the same material as the balloon.

36. An intragastric balloon assembly according to claim 34, further comprising a foldable plastic screen, disposed around the rigid support and spaced apart from the balloon, and integrally formed with the rigid support, said foldable plastic screen being capable of being initially in a folded position, before inserting the balloon assembly into the stomach, and capable of being spread out after crossing the stomach wall, said screen being configured to lay over a stomach external wall and attach thereon to seal an area of the hole formed in the stomach to prevent gastric juices from leaking.

37. An intragastric balloon assembly according to claim 36, wherein the foldable plastic screen, is made of silicon.

38. A procedure to set the intragastric balloon of claim 22 to treat a patient suffering from obesity, comprising the steps of:

applying asepsis and antisepsis measures;

anesthetizing the patient under an anesthesiologist surveillance;

placing the patient in a ventral decubitus position;

performing an abdomen antisepsis;

setting sterile fields to limit superior hemiabdomen;

introducing a central view flexible endoscope through a mouth of the patient;

identifying stomach of the patient inflated with air by means of the endoscope;

pressing a bottom of a gastric body against a major curvature with the endoscope, to identify a puncture site by locating light through the abdominal wall;

applying local anesthesia with diluted xilocaine without epinephrine at a puncturing site;

making a small incision with a 2 mm knife;

introducing a puncturing trocar at the puncturing site, by piercing all layers of the abdominal wall and perforating the stomach, watching this operation through the endoscope;

removing a pointed mandrin from trocar;

introducing into the stomach a resistant suture through the light of trocar;

taking the suture with the pliers of an endoscope taking away the endoscope together with the suture through the mouth;

tying the suture to the handle of the rigid support;

making traction of the suture through the abdominal wall so that the rigid support along with the balloon and catheter are carried throughout a digestive tube to the stomach, the rigid support being taken through the gastric wall and the abdominal wall;

inflating the balloon through detachable catheter that is partially exposed at that time through the patient's mouth to a partial volume of about 200 to 300 cc that allows exerting tension between the rigid support and the inflated balloon, so as to close the perforated stomach wall to the parietal peritoneum layer;

separating the inflating catheter from the balloon;

removing percutaneous trocar;

carrying out a surgical incision of 5–7 cm;

cutting the skin and cellular tissue up to the aponeurosis;

dissecting aponeurosis surface to place the fixing plate on this site;

making traction on the rigid support for the balloon to be attached to the gastric wall and the gastric wall in turn to be adhered to abdominal wall at the peritoneal layer to avoid leakage of gastric content to the abdominal wall;

fixing the rigid support and introducing the rigid support through hole, cutting excess of the rigid support and fixing the rigid support to flange by a suture;

fixing the fixing plate to the anterior aponeurosis of the abdomen by suture through fixing holes;

closing the subcutaneous cellular tissue and the skin.

39. A surgical procedure according to claim 38 including the step of applying a layer of a material promoting fibrosis and cicatrisation over the rigid support and the balloon on the regions having contact with the tissues, once they have been taken to the stomach of the patient.

40. A surgical procedure according to claim 38 taken in combination with the intragastric balloon assembly of claims 34 to 37, including the steps of: spreading out the foldable screen once the area of rigid support bearing screen has crossed the stomach wall so that said screen lays over the stomach external wall and is attached thereon sealing the area of the hole formed in the stomach to prevent gastric juices from leaking.

41. An intragastric balloon assembly for reducing food intake of a person suffering from obesity, comprising:

a balloon;

a tubular member for attaching the balloon to a gastric wall of a stomach of a person, the tubular member including a first end affixed to the balloon and a second end affixed to a handle;

a catheter detachably connected to the balloon and configured to inflate the balloon; and an inflation valve connected to the catheter.

42. The intragastric balloon assembly of claim 41, wherein the catheter is disposed adjacent the tubular member.

43. The intragastric balloon assembly of claim 41, a first end of the catheter is joined to the balloon and a second end of the catheter is connected to the inflation valve.

44. The intragastric balloon assembly of claim 41, wherein the second end of the tubular member is configured to be anchored against a portion of an abdominal wall of the person to thereby attach the balloon to the gastric wall of the stomach of the person.

45. The intragastric balloon assembly of claim 44, wherein tubular member is configured to be anchored against the portion of the abdominal wall with a plate member.

46. The intragastric balloon assembly of claim 41, wherein the inflating valve comprises a self-sealing valve disposed in a wall of the balloon.

47. The intragastric balloon assembly of claim 46, wherein the catheter is connected to the balloon at the self-sealing valve.

48. The intragastric balloon assembly of claim 41, wherein the catheter is connected to the balloon at a location diametrically opposite a location where the tubular member is affixed to the balloon.

49. The intragastric balloon assembly of claim 41, wherein the inflation valve includes a central aperture through which the tubular member is received.

50. A method of installing an intragastric balloon assembly in a stomach of a patient, comprising the steps of:

providing the intragastric balloon assembly including a tubular member having a first end affixed to a balloon and a second end affixed to a handle, a catheter detachably connected to the balloon, and an inflation valve connected to the catheter;

identifying the stomach using the endoscope introduced through a mouth of the patient;

identifying a puncture site on a portion of an exterior portion of an abdominal wall of the patient;

piercing all layers of the abdominal wall at the puncture site and perforating the stomach to thereby introduce a first end of a suture into the stomach;

grasping the first end of the suture with the endoscope and pulling the endoscope and the first end of the suture through the mouth of the patient;

attaching the first end of the suture to the handle of the intragastric balloon assembly;

pulling a second end of the suture so that the first end of the suture, the intragastric balloon assembly is pulled into the stomach, and the tubular member and the catheter are pulled through the gastric wall and the abdominal wall;

inflating the balloon with a fluid through the catheter; and fixing the tubular member and the catheter to the abdominal wall with a fixing plate to thereby secure the balloon against the gastric wall of the stomach of the patient.

* * * * *